United States Patent [19]
Kronberg et al.

[11] Patent Number: 5,273,036
[45] Date of Patent: Dec. 28, 1993

[54] APPARATUS AND METHOD FOR MONITORING RESPIRATION

[75] Inventors: Harald Kronberg, Staufen; Helmut Leist, Waldkirch, both of Fed. Rep. of Germany

[73] Assignee: PPG Industries, Inc., Pittsburgh, Pa.

[21] Appl. No.: 49,965

[22] Filed: Apr. 20, 1993

Related U.S. Application Data

[63] Continuation of Ser. No. 985,533, Dec. 3, 1992, abandoned, which is a continuation of Ser. No. 679,696, Apr. 3, 1991, abandoned.

[51] Int. Cl.[5] .............................................. A61B 5/00
[52] U.S. Cl. ................................... 128/633; 128/666; 128/716
[58] Field of Search ........................ 128/633, 665–666, 128/716; 364/413.03

[56] References Cited

U.S. PATENT DOCUMENTS

| | | | |
|---|---|---|---|
| Re. 30,317 | 7/1980 | Lubbers et al. | 128/635 |
| 3,152,587 | 10/1964 | Ullrich et al. | 128/2 |
| 3,704,706 | 12/1972 | Herczfeld et al. | 128/633 |
| 4,407,290 | 10/1983 | Wilber | 128/633 |
| 4,765,340 | 8/1988 | Sakai et al. | 128/716 |
| 4,867,165 | 9/1989 | Neller et al. | 128/633 |
| 4,880,304 | 11/1989 | Jaeb et al. | 128/633 |
| 4,926,867 | 5/1990 | Kanda et al. | 128/633 |
| 4,936,309 | 6/1990 | Cooper | 128/716 |

FOREIGN PATENT DOCUMENTS

| | | |
|---|---|---|
| 0071980 | 2/1983 | European Pat. Off. . |
| 0247777 | 12/1987 | European Pat. Off. . |
| 2423441 | 11/1975 | Fed. Rep. of Germany . |
| 2604890 | 4/1988 | France ........................ 128/666 |
| 987504 | 3/1965 | United Kingdom . |
| 2116725 | 9/1983 | United Kingdom . |

OTHER PUBLICATIONS

Anderson, F. A., Jr.; "Impedance Plethysmography" in *Encyclopedia of Medical Devices and Instrumentation*, John Wiley & Sons, 1988, vol. 3, pp. 1641–1643.

R. Allen, "Intracranial Pressure: A Review of Clinical Problems, Measurement Techniques and Monitoring Methods", *Journal of Medical Engineering & Technology*, vol. 10. No. 6, Nov./Dec., 1986, pp. 299–320.

Y. Mendelson and B. D. Ochs, "Noninvasive Pulse Oximetry Utilizing Skin Reflectance Photoplethysmography", *IEEE Transactions of Biomedical Engineering*, vol. 35, No. 10, Oct. 1988, pp. 798–805.

*Primary Examiner*—Lee S. Cohen
*Assistant Examiner*—Robert C. Nasser, Jr.
*Attorney, Agent, or Firm*—Andrew C. Siminerio; Kenneth J. Stachel

[57] ABSTRACT

The apparatus for monitoring respiration comprises a photoplethysmographic sensor whose LED transmitter element(s) is/(are) excited by a monitoring unit with a specified control power and/or control signal sequence or frequency. By means of a signal processing unit, both the frequency and depth of respiration can be measured, as can the pulse frequency or oxygen saturation of the peripheral blood. The use of such an apparatus guarantees significantly more reliable monitoring of respiration than the impedance pneumographic methods of the prior art.

19 Claims, 3 Drawing Sheets

APPARATUS AND METHOD FOR MONITORING RESPIRATION

This application is a continuation of U.S. application Ser. No. 07/985,533, filed Dec. 3, 1992, now abandoned, which is a continuation of U.S. application Ser. No. 07/679,696, filed Apr. 3, 1991, now abandoned.

This invention relates to an apparatus and method for monitoring respiration by the peripheral measurement of vital signs relevant to respiration.

The measurement of respiration is one of the basic requirements of intensive medical monitoring and diagnosis. While there are very satisfactory measurement methods for intubated patients or patients wearing a breathing mask, the problems regarding non-invasive monitoring of respiration relating to operation, reliability, accuracy and repeatability of the measurements have not previously been solved satisfactorily. Respiration sensors based on a thermistor in the respiratory path in front of the mouth and/or nose are difficult to apply, and are frequently not tolerated by the patient. Breathing belts around the chest and abdomen for mechanical pulmonary plethysmography require a great deal of care, additional wires on the patient and patient monitoring devices (see British Pat. No. 2,116,725 which teachings are incorporated by reference).

It is known that during respiration, there are synchronous periodic fluctuations of the volume of blood in all body compartments, partly as a consequence of oxygenation-synchronous blood pressure modulation, but primarily on account of mechanical pressure and pumping action. Thus, for example, intracranial pressure increases during expiration on account of venous blood backpressure (see R. Allen, "Intracranial pressure; A review of clinical problems, measurement techniques and monitoring methods", *J. Med. Engng. + Techn.*, 10 (1986), 299-320, which teachings are incorporated by reference). There is a pronounced displacement of the blood in the surface of the thorax during inspiration. For this reason, impedance pneumography is currently in common use to monitor respiration, which employs EKG chest electrodes to measure the modulation by approximately 1 mil (1 thousandth) of the thorax impedance which occurs as a result of respiration (see F. A. Anderson Jr., "Impedance Plethysmography", *Encyclopedia of Medical Devices and Instrumentation*, Vol. 3, ed. J. G. Webster, (John Wiley+Sons, 1988), pp. 1641-1643, which teachings are incorporated by reference). Unfortunately, this weak respiration signal is subject to interference by artifacts, a base line drift which is a function of the position of the body, and with conventional two-conductor measurement technology, to interference from local electrode skin transition impedances. Of course, impedance pneumography using two-conductor measurement technology requires hardly any increased operational effort besides the EKG recording, but a satisfactory monitoring of respiration can generally only be achieved with additional electrodes attached to the patient and using four-conductor measurement technology. A fundamental disadvantage of this measurement method is that a measurable respiratory movement is by no means a sign of effective respiration. For example, there may be obstructions in the respiratory path or uncoordinated, out-of-phase chest and abdominal respiration in premature infants with respiratory systems not yet fully developed.

The object of the invention is therefore to improve the non-invasive monitoring of respiration with regard to clinical ease of operation, reliability and repeatability of the measurement results. The invention provides an apparatus and method for monitoring respiration by the peripheral measurement of vital signs relevant to respiration, and is characterized by a sensor to be applied on the surface of an organ containing blood vessels, preferably in the vicinity of the upper part of the patient's body. The sensor contains a radiation transmitter which emits electromagnetic radiation into the organ tissue, and a radiation receiver which receives a portion of the radiation after the radiation has interacted with the organ tissue. A control unit excites the radiation transmitter with a desired control output, control signal sequence and control signal sequence frequency. A signal processing unit receives the signal output from the radiation receiver and prepares at least one output signal corresponding to the temporal sequence of respiratory excursion and/or determines frequency and/or depth of respiration.

Compared to the impedance pneumographic respiration monitoring method of the prior art, the apparatus and method for monitoring respiration according to the invention, even in its very simplest embodiment which measures only the frequency of respiration, has the great advantage of an essentially stable and interference-proof measurement signal.

There is a significant improvement of respiratory monitoring, in particular in the event of obstructed or uncoordinated respiration, if the respiration monitoring apparatus defined above is combined with a pulse oximeter of the prior art (see U.S. Pat. No. 4,407,290 which teachings are incorporated by reference). In addition to the conventional pulse oximetric measurement of arterial oxygen saturation and pulse frequency, respiration is then monitored without any additional effort on the part of the operator, so that weak or incomplete respiratory excursions can be detected by the decrease in the oxygen saturation of the hemoglobin, and an alarm can be given. In this combination, the radiation transmitter contained in the sensor is sequentially excited at at least two wavelengths in the visible and near infrared range, e.g. 660 nm and 940 nm, and its output signal is evaluated in the manner of the prior art for a determination of the oxygen saturation and pulse frequency in the signal processing unit. The prior art includes various methods for the photoplethysmographic measurement of peripheral local blood circulation. Depending on the type of measurement being conducted, transmission or reflection sensors are used for this purpose (see, for example, U.S. Pat. No. 3,152,587 and British Patent No. 987,504 which teachings are incorporated by reference). If an infrared radiation source is used for the photoplethysmography with isosbestic wavelength of 805 nm for hemoglobin and oxyhemoglobin, the measurement signal is independent of the oxygen saturation of the blood. Heretofore, however, such sensors have been used only to monitor pulse frequency, while other signal components were merely suppressed as interference.

In the context of dual wavelength pulse oximetry, however, processes have also been developed to quantify blood perfusion near the surface of the body which no longer use an isosbestic wavelength (see European Patent 0 293 504 which teachings are incorporated by reference). With these processes, however, it is possible to measure only a gradual change in perfusion, e.g. during operations.

The prior art also includes methods to measure similar perfusion values calorimetrically. For this purpose, transcutaneous blood gas sensors attached to the skin can be used, which are equipped with a heating system for the hyperemization of the arterial capillary bed. From the heating output required for a constant hyperthermal skin temperature, the perfusion efficiency and the perfusion pressure can then be obtained (See German Patent Nos. 22 55 879 and 24 23 441 which teachings are incorporated by reference).

One of the ideas on which the present invention is based in the use of measurement methods and systems of the prior art to measure perfusion changes which are synchronous with respiration. Heretofore, neither the photoplethysmographic nor the calorimetric methods have been used to monitor respiration.

The apparatus and method according to the invention could also be called a photoplethysmographic monitoring system, which can advantageously be equipped with additional measurement probes or sensors for the simultaneous monitoring of additional vital signs, such as the blood gas partial pressure of the arterial blood, peripheral blood perfusion and/or subsurface body temperature, which are frequently necessary.

The invention and advantageous details are explained in greater detail below, with reference to the embodiment illustrated by way of example in the accompanying drawings.

FIGS. 1 and 3 show photoplethysmographic reflex sensors, as they can advantageously be used in combination with the invention.

FIGS. 2 and 4 are views taken along line 2—2 of FIG. 1 and line 4—4 of FIG. 3, respectively.

Figure 1:
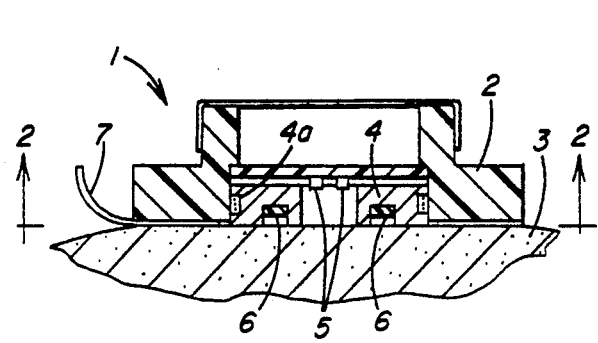

FIGS. 1 through 4 show, by way of example, two different embodiments of photoplethysmographic reflex sensors 1 which can be attached directly to an organ surface 3, for example by means of adhesive ECG electrode rings 7, preferably on the skin of the torso in the vicinity of the sternum, the chest muscles, on or between the shoulder blades. Light-emitting diodes (LEDs) 5 are used as the radiation source, whereby two or more such LEDs can be used for the additional measurement of predetermined blood components. The modified radiation component received from the tissue is picked up by photodiodes (PHDs) 6 as the receivers, which are located at the optimum distance of approximately 3 mm to 15 mm from one another inside a heater 4, surrounded by a fixing ring 2, which is simultaneously used to absorb interference radiation. The heater 4, as indicated, is heated by means of a rotating resistance wire coil 4a or cemented heating resistances.

Figure 5:
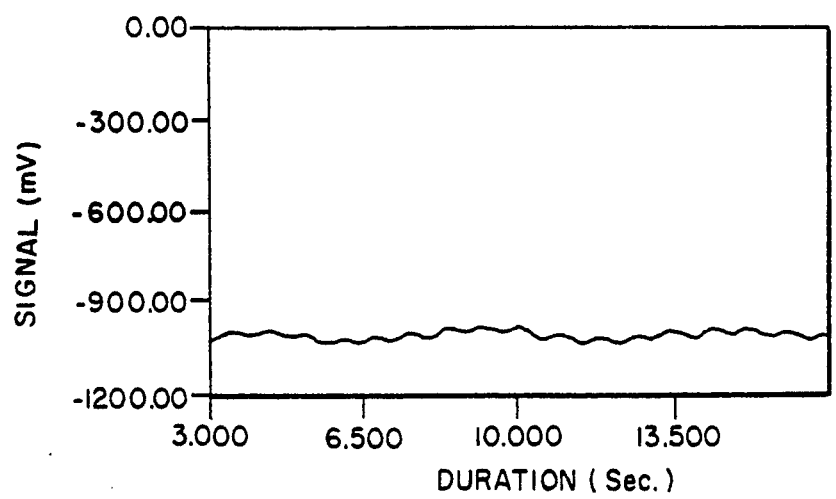
FIG. 5 is a diagram of a typical measurement signal of a sensor as illustrated in FIG. 1 or FIG. 3, at the output of a preamplifier.

FIG. 5 shows a typical infrared measurement signal at the output of a preamplifier. The measurement value of approximately −1000 mV is modulated with signal fluctuations which are pulse-synchronous (e.g. 72 pulse beats/minute) and respiration-synchronous (e.g. 11 breaths/minute). The amplitude of the superimposed alternating current voltage component is proportional to the mean signal, so that for the further signal processing, only relative alternating currents (quotient of AC and DC portion) with reference to this mean value are of interest. The amplitudes are on the order of 1%, in relation to the mean signal in FIG. 5. Therefore they are significantly more resistant to interference than the signal from a thorax impedance measurement.

For a photometric optimization of the signal processing, the alternating current component can be standardized to the signal peaks, but as noted above, the latter normally differ by only about 1% from the mean value. To suppress artifacts, therefore, it is appropriate to determine the mean value of the measurement or averaged peak values over a flexible time window.

In the context of the tests conducted during development of the invention, it was determined that the relative alternating current voltage increases as the heating temperature is increased between 37° C. and 44° C., and also increases with the distance between the LEDs 5 and the photodiodes 6.

Figure 2:
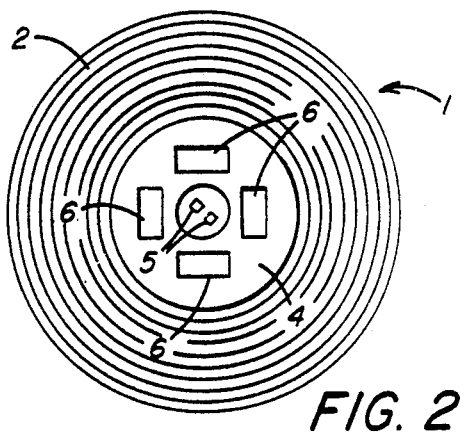
Figure 3:
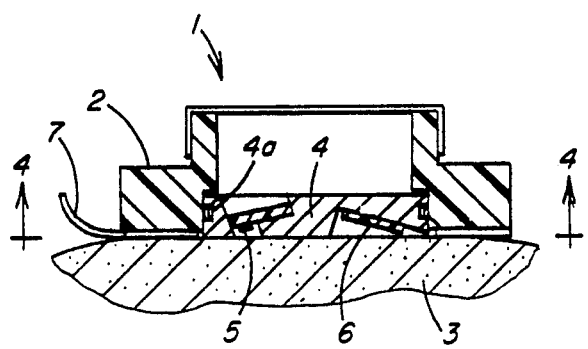
Figure 4:
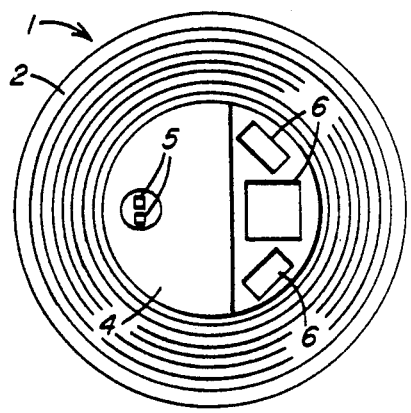

Compared to the embodiment illustrated in FIGS. 1 and 2, the reflex sensor illustrated in FIGS. 3 and 4 has a greater LED-PHD distance with an asymmetrical arrangement of the transmitter and receiver elements, but the overall size remains the same. To optimize the signal, the LEDs 5 and the PHDs 6 can also be arranged at a specified setting angle to the surface of the tissue 3, which is shown in the detail in the left portion of FIG. 3.

Figure 9:
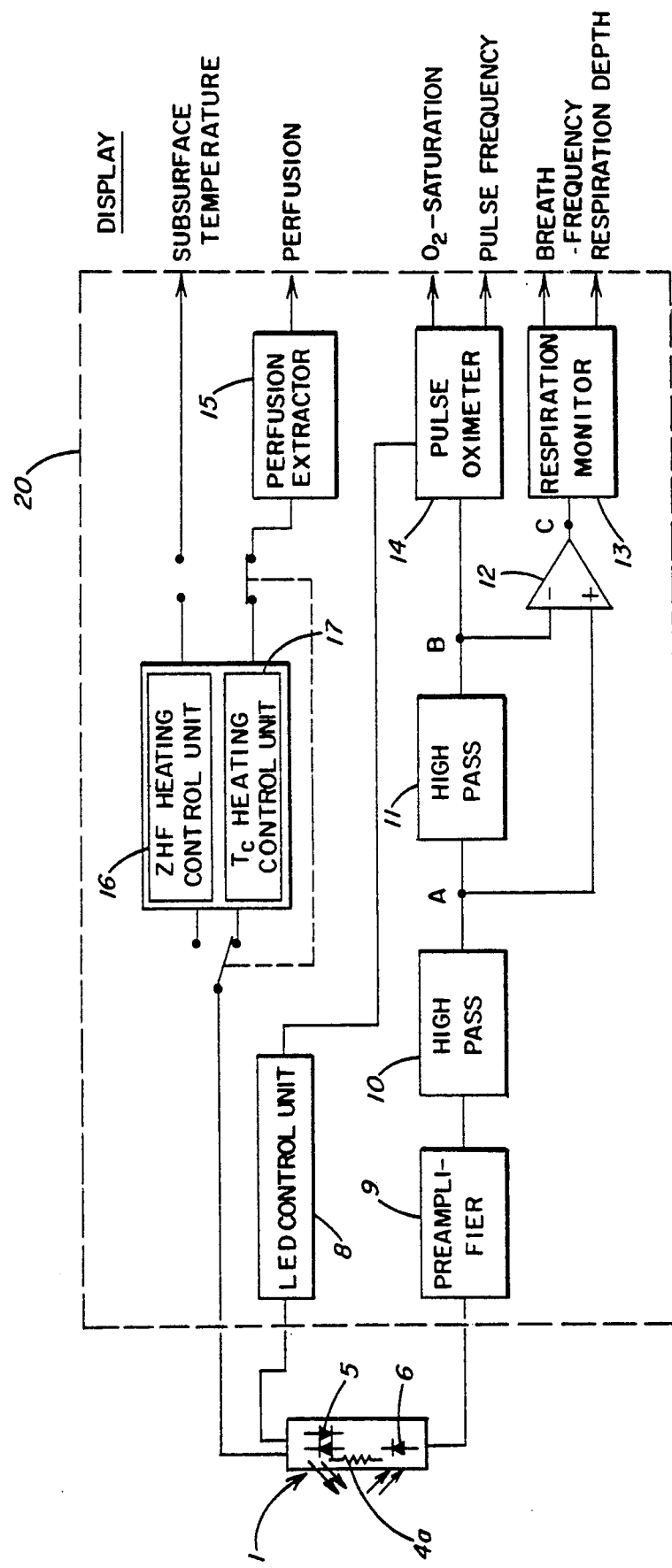
FIG. 9 is a schematic diagram of a complete respiration monitoring apparatus, by means of which even more vital signs can be advantageously obtained and displayed.

FIG. 9, for example, shows the block diagram of a monitoring apparatus 20 according to the invention, to which the sensor 1 is attached. After preamplification and impedance transformation in the preamplifier 9, and elimination of a slow signal drift in a high pass 10, the signal as observed at Point A of FIG. 9 is shown in FIG. 5, which still contains all the spectral components above ten periods/min. In the measurement signal in FIG. 5, a reflex sensor shown in FIG. 3 was attached to the sternum of a patient who was breathing on his own, and the underlying capillary bed in the tissue 3 was hyperemized for 10 minutes at 44° C. The diagram in FIG. 6 shows, as the measurement signal in question, the relative AC voltage obtained at Point A of the circuit in FIG. 9, normalized to the DC component.

To determine all the vital measurements which can be obtained from the arterial pulse (e.g. pulse perfusion at 805 nm—single wavelength photometry, pulse frequency, plus oxygen saturation of the hemoglobin with at least two wavelengths photometry by means of a pulse oximeter 14), low frequency signal changes caused by respiration are eliminated in an additional high pass 11.

Figure 6:
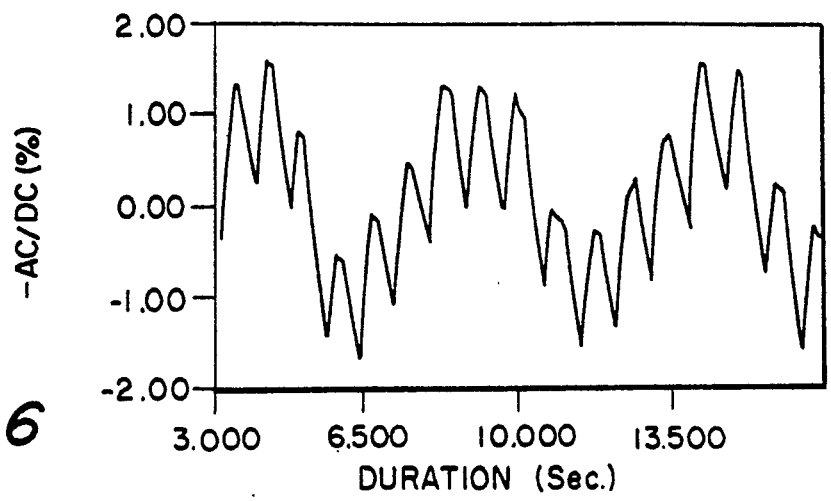
FIG. 6 shows an advantageous measurement signal which contains three signal components, namely frequency of respiration, depth of respiration and pulse frequency.
Figure 7:
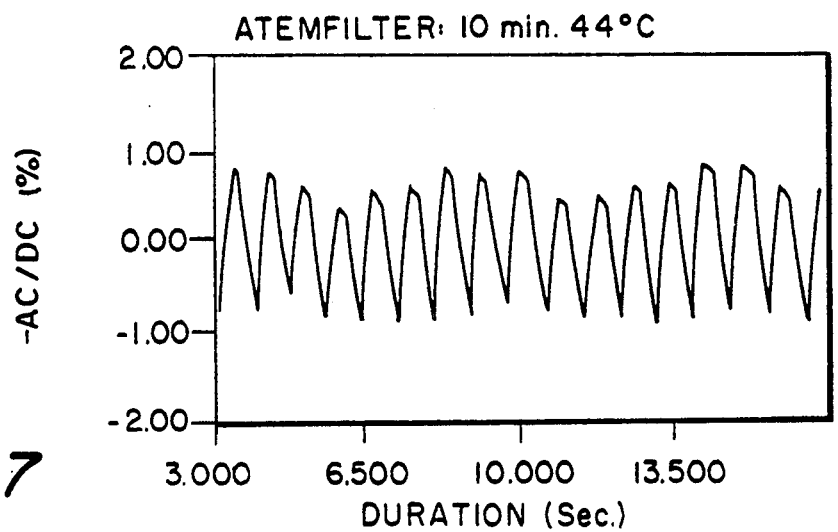
FIG. 7 shows the measurement shown in FIG. 6 with the pulse signal filtered out.

FIG. 7 shows the relative AC voltage at Point B of the circuit illustrated in FIG. 9, if all the spectral components less than 36 periods/minute of the signal are filtered out at Point A (see FIG. 6).

Figure 8:
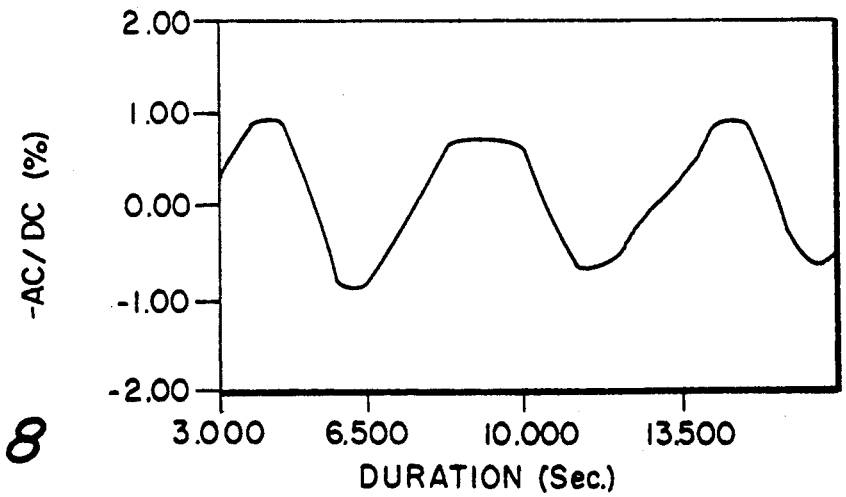
FIG. 8 shows the measurement shown in FIG. 6 with the respiration signal filtered out.

At Point C, namely after a combination of the signals at the Points A and B by means of a difference amplifier 12, there appears at the input of a respiration monitor 13 a respiration signal which can be easily evaluated as the difference of the voltages at Points A and B, with a relative alternating current voltage as shown in FIG. 8, from which the frequency of breathing and the depth of breathing can be obtained in a known manner, similar to impedance pneumography.

The block diagram in FIG. 9 shows two sensor control connections, on one hand for the operation of the LEDs 5 by means of an LED control unit 8 assigned to the pulse oximeter 14, and on the other hand for the sensor heating by means of a switchable heating unit 16, 17. If the sensor 1 for the hyperemia is heated by the pulse oximeter 14 to a constant temperature $T_c$, it is possible that the perfusion extractor 15 also connected in the illustrated embodiment will determine the local organ perfusion both calorimetrically by means of the heating control and also photometrically by means of the measurement signal branch 9-10-11-14, and if necessary can even exercise control by comparison. The heating means of the sensor and said single processing unit can include a temperature control which heats said surface tissue of said organ at the application point of said sensor to a temperature corresponding to the subsurface body temperature and can also include a means to display said subsurface body temperature.

It is also possible to switch to an alternative sensor heater 16, to also measure the subsurface body temperature by means of a measurement method which was proposed as the "zero heat flow" method (See European Patent Application No. 89 109 162.1 which teachings are incorporated by reference).

For pulse oximetry when the measurement uses at least two wavelengths, the block diagram in FIG. 9 is executed in multichannel fashion in the measurement branch 9-10-11-14, as will be apparent to a technician skilled in the art. If, moreover, the reflex sensor (FIG. 3) is combined with additional sensor components, e.g. with electrodes for transcutaneous blood gas monitoring, then the monitoring device will also contain an appropriate combination of function circuits.

The information in FIG. 9 on the filter frequencies should not be interpreted rigidly. Of course, the pulse frequency and breathing frequency can almost always be easily separated, since they are generally in the ratio of 4:1. In an advantageous extension of the theory behind the invention, however, it is also appropriate to adjust the cut-off frequencies to the age of the patient since, for example, the pulse and breathing frequencies of a newborn are approximately three times higher than those of an adult.

An additional possibility for measuring respiration from the known respiratory pulse frequency arrhythmia (the pulse frequency increases during inspiration) is not illustrated in the block diagram of the monitoring device according to the invention illustrated in FIG. 9. Such a capability would be realized by means of digital signal processing and pattern recognition.

We claim:

1. An apparatus for monitoring respiration of a patient by peripheral measurement of vital factors relevant to respiration, comprising:
   a sensor to be applied on a surface tissue of an organ containing blood vessels; said sensor including;
   at least one radiation transmitter means which emits electromagnetic radiation into the organ tissue, and
   at least one radiation receiver means which receives a portion of the radiation after the radiation passes through the organ tissue and blood components and generates an output signal;
   a control means which excites said radiation transmitter with a desired control output, control signal sequence and control signal sequence frequency; and
   a means for signal processing which receives said signal output from said radiation receiver means and determines therefrom measurements for the patient's respiratory activity of at least one of the following: temporal curve of the respiratory excursion, the frequency, and the depth of respiration.

2. The apparatus according to claim 1 wherein said control means includes means to excite said radiation transmitter means to emit electromagnetic radiation on at least two different frequencies (wavelengths), said radiation receiver means delivers output signals for said at least two radiation frequencies received after passing through said organ tissue and blood components, and said means for signal processing also can determine at least one of the following: 1) measurements for the specified blood components, and 2) blood circulation values based on said output signals.

3. The apparatus according to claim 2 wherein said means for signal processing includes a pulse oximeter means for the determination of at least the oxygen saturation of the peripheral arterial blood in the organ tissue.

4. The apparatus according to claim 2 wherein the means for signal processing can determine the pulse frequency as a blood circulation value.

5. The apparatus according to claim 2 wherein said means for signal processing includes a bandpass filter selected from the group consisting of: fixed bandpass filters, adjustable bandpass filters, and bandpass filters with automatically adaptable cutoff frequencies.

6. The apparatus according to claim 5 wherein said cutoff frequencies of said bandpass filter are selected in the range of 8 to 50 periods/min. and approximately in the ratio 4:1.

7. The apparatus according to claim 1 wherein said means for signal processing includes a high pass filter means to eliminate gradual signal drift.

8. The apparatus according to claim 1 wherein said means for signal processing includes a preamplifier means to normalize said output signals to values selected from the group consisting of: their mean values and peak values.

9. The apparatus according to claim 8 wherein said preamplifier means normalizes to values selected form the group consisting of: means values and peak values measured over moving limited time segments.

10. The apparatus according to claim 1 wherein said radiation transmitter means is a light emitting diode of a specified radiation frequency (radiation wavelength) in the visible and near-infrared range.

11. The apparatus according to claim 10 wherein said light emitting diode radiates at a radiation frequency of approximately 805 nm.

12. The apparatus according to claim 1 wherein said radiation receiver means is a photodiode with spectral sensitivity adapted to the radiation frequency (wavelength) of the radiation transmitter.

13. The apparatus according to claim 1 wherein said sensor includes a heating means and said means for signal processing includes means to provide for the thermostatic control of said sensor to the hyperemization temperature of adjacent bodily tissue.

14. The apparatus according to claim 13 wherein said means for signal processing includes means to display a measurement for blood perfusion derived by heating the sensor to a constant temperature and making the determination calorimetrically.

15. The apparatus according to claim 1 wherein said sensor includes a heating means, and said means for signal processing includes a temperature control which heats said surface tissue of said organ at the application point of said sensor to a temperature corresponding to the subsurface body temperature and means to display said subsurface body temperature.

16. A method of monitoring respiration of a patient by peripheral measurement of vital factors relevant to respiration, comprising:
    applying a sensor to the surface tissue of an organ containing blood vessels;
    emitting electromagnetic radiation at a desired control output, control signal sequence and control signal sequence frequency, from said sensor into the organ tissue;
    receiving a portion of said radiation after said radiation passes through said organ tissue and blood components;
    generating an output signal based on said received portion of said radiation; and
    processing said signal output to determine from the received portion of the radiation measurements for the patient's respiratory activity of at least one the of the following: temporal curve of the respiratory excursion, the frequency, and the depth of respiration.

17. The method according to claim 16 wherein said emitting step includes the step of emitting electromagnetic radiation on at least two different frequencies (wavelengths), said generating step includes the step of generating output signals for the at least two radiation frequencies received after passing through said organ tissue and said processing step includes at least one of the steps of determining measurements for the specified blood components, and determining blood circulation values.

18. The method according to claim 17 wherein said emitting step includes the step of emitting radiation from light emitting diodes of a specified radiation frequency (radiation wavelength) in the visible and near-infrared range and said receiving step includes the step of receiving said portions of said radiation with photodiodes with spectral sensitivities adapted to the radiation frequencies (wavelengths) of said light emitting diodes.

19. The method according to claim 18 further including the steps of heating the surface tissue of said organ at the application point of said sensor to a temperature corresponding to the subsurface body temperature and displaying said subsurface body temperature.

* * * * *